United States Patent [19]

Sluss, Jr. et al.

[11] Patent Number: 5,348,019

[45] Date of Patent: Sep. 20, 1994

[54] OPTICAL FIBER PRESSURE SENSING CATHETER

[75] Inventors: James J. Sluss, Jr., Norman; James C. Duke, Oklahoma City; Kevin R. Lewelling, Noble, all of Okla.; Shaun L. Harris, Allen, Tex.

[73] Assignee: The Board of Regents of the University of Oklahoma, Norman, Okla.

[21] Appl. No.: 947,209

[22] Filed: Sep. 18, 1992

[51] Int. Cl.$^5$ .............................................. A61B 5/02
[52] U.S. Cl. ................................... 128/667; 128/675; 73/705; 73/862.624
[58] Field of Search ............... 128/748, 774, 780, 673, 128/672, 675, 667, 634; 73/705, 862.624; 250/231.19

[56] References Cited

U.S. PATENT DOCUMENTS

| | | | |
|---|---|---|---|
| 4,435,174 | 3/1984 | Redmond et al. | 604/174 |
| 4,703,757 | 11/1987 | Cohen | 128/667 |
| 4,735,212 | 4/1988 | Cohen | 128/667 |
| 4,787,396 | 11/1988 | Pidorenko | 128/667 |
| 4,803,992 | 2/1989 | Lemelson | 128/634 |
| 4,924,877 | 5/1990 | Brooks | 128/748 |
| 4,936,310 | 6/1990 | Engström et al. | 128/673 |
| 4,991,590 | 2/1991 | Shi | 128/667 |
| 5,018,529 | 5/1991 | Tenerz et al. | 128/667 |
| 5,187,983 | 2/1993 | Bock et al. | 73/705 |
| 5,195,375 | 3/1993 | Tenerz et al. | 73/705 |

OTHER PUBLICATIONS

J. Schneider, H. Modler, R. Kist, H. Wolfelschneider, and H. D. Becker; The Fibre Fabry Perot Sensor. A Long-term Manometry Sensor for Quantitative Intraluminal Pressure Measurement of the Gatrointestinal Tract, *Clin. Phys. Physiol. Mess.*, 1990, vol. 11, No. 4, 319-325.

*Primary Examiner*—Stephen C. Pellegrino
*Assistant Examiner*—Guy V. Tucker
*Attorney, Agent, or Firm*—Dunlap Codding Lee

[57] ABSTRACT

An optical fiber pressure sensing catheter and a method for using such for detecting a discrete pressure within an organ such as an esophagus. The catheter comprises an elongated hollow body having a wall, a closed proximal end, a closed distal end, and a lumen therebetween. The wall is generally noncompressible by pressure normally exerted thereupon by the organ within which the catheter is inserted except for at least one discrete sensing area of the wall having sufficient flexibility so as to be compressible by pressure exerted thereupon by the organ within which the catheter is inserted. The catheter further comprises at least one sensing optical fiber disposed within the lumen. The optical fiber further comprises a pressure sensing means which is a portion of the optical fiber adjacent the discrete sensing area of the wall. The sensing portion is deformable in response to compression of the discrete sensing area of the wall, which deformation causes attenuation of light transmitted through the fiber. The catheter may further comprise a reference optical fiber disposed within the lumen of the body for use as a comparator with the sensing optical fiber. The catheter may further comprise a positioning assembly disposed within the lumen adjacent the discrete sensing area of the wall for positioning the sensing portion of the sensing optical fiber in a sensing position. The catheter may comprise a plurality of optical fibers and a plurality of discrete sensing areas.

49 Claims, 4 Drawing Sheets

OPTICAL FIBER PRESSURE SENSING CATHETER

BACKGROUND OF THE INVENTION

1. Field of the Invention

The present invention relates to optical fiber catheter systems and methods for measuring intralumenal pressures of internal organs and more particularly, but not by way of limitation, to optical fiber catheters and methods used for evaluating dysfunctions of the gastrointestinal tract by measuring motility of various portions of the alimentary and gastrointestinal tract.

2. Brief Discussion of the Related Art

There are many problems and dysfunctions associated with the gastrointestinal tract. Dysfunctions are diagnosed using manometry in which pressure transducers are used to measure contraction pressure (i.e. esophageal motility and colonic motility) within the esophagus. Symptoms of a dysfunctional esophagus can be manifested in many ways, including heartburn, gastric emptying (food being forced back into the esophagus from the stomach), and chest pains (appearance of cardiac problems). Any mechanical obstruction of the esophageal lumen can cause discomfort in eating and sleeping. Obstructions can range from interesophageal lesions caused by cancer or peptic structure to irregular esophageal peristalsis (wave-like motion of the esophagus) resulting in delayed clearance of the esophagus. These problems are caused by a variety of neural and muscular defects. There are several well documented motility disorders, including achalasia, diffused esophagus spasm (DES), hypertensive lower esophagus, nutcracker esophagus, scleroderma, diabetes mellitus and presbyesophagus.

There are two pressure measuring catheters commonly used today: water perfused catheters and solid state catheters.

Water perfused Catheters

A water perfused catheter consists of a flexible tube containing several lumens. Each lumen is filled with water. Water is used because it is a noncompressible fluid and is not harmful when pumped into the esophageal body. Each lumen has a side hole through which water, at different points along the catheter, is ejected. As the esophagus contracts, the hole is obstructed causing the pressure to rise in the lumen. The pressure rises until it forces the obstructed side hole open. The pressure at which this event occurs corresponds to the esophageal pressure. It is possible to make circumferential pressure measurements with this system, which allows a cross-sectional view of pressure readings at one level in the esophagus.

Solid State Transducer Catheter

The solid state transducer catheter uses a flexible diaphragm to transfer the esophageal pressure from the exterior to the transducer. Since these transducers are located at defined locations along the length of catheter, a more accurate point pressure reading is possible. The change in pressure causes a change in the transducer voltage. This relationship is used to deduce the esophageal pressure.

Water Perfused Catheter vs Transducer Catheter

The best solid state transducer catheters have three or four sensing points while the water perfused catheters have eight or more. The apparent advantage of the water perfused catheter is diminished because the esophagus must remain level with the external transducer when using the water perfused catheter. The water perfused catheter forces the patient to lie down and remain supine during the motility study. Also, there are problems with air bubbles in the water perfused catheter which cause a reduction of sensitivity. This is not the case if the transducer catheter is used, as the patient is free to sit or recline while the study is being performed. The water perfused catheter requires a supply of sterile water to be readily available. It also requires an extensive cleaning procedure which not only cleans the exterior of the catheter, but each lumen within the catheter.

The transducer catheter is limited to three or four point measurements which must be used to statistically reconstruct a volumetric representation of the esophageal responses. The water perfused catheter has eight or more points of pressure measurement, but has a slower response to rapid transient changes in pressure. Both catheter types have an external diameter of approximately 5 mm.

A third instrument which has been studied for use in the measurement and recording of intraesophageal pressure is the Fibre-Fabry-Perot (FFP) sensor. This is a U-shaped 30 micrometer diameter optical fiber embedded in a silicone rubber probe. The instrument operates on the principle of mirror interferometry in which changes of optical length result in changes of face—independent light intensity which provide a signal proportional to the force of the intraluminal contraction.

Today, optical fibers are commonly used in communication systems and many other applications. Although fiber optic systems are very fast and have low loss, there are three primary loss mechanisms (attenuation factors) associated with optical fiber which degrade the optical signal power: rayleigh scattering, absorption, and microbending loss. Rayleigh scattering is due to minute inhomogeneities in the core material of the fiber. As the light propagates along the length of the fiber, it encounters minute defects which scatter the optical power in all directions. As a result, power loss is noticed at the detector. Absorption of optical power is due to the presence of impurities in the fiber core. Microbending loss accounts for the other attenuation factor. This loss mechanism is due to the change in geometry of the fiber as a result of bending. As the fiber is bent the optical power residing in the cladding (evanescent field), on the outside edge of the bend, must traverse a longer distance. The propagation velocity of this evanescent field cannot exceed the speed of light, so it is coupled out and lost. Microbending loss is the physical phenomenon underlying the optical power attenuation relied upon in the present invention to detect pressure changes.

SUMMARY OF THE INVENTION

The present invention is an optical fiber pressure sensing catheter and a method for using such for detecting a discrete pressure within an organ. The catheter comprises an elongated hollow body having a wall, a closed proximal end, a closed distal end, and a lumen therebetween. The wall is generally noncompressible by pressure normally exerted thereupon by the organ within which the catheter is inserted except for at least one discrete sensing area of the wall having sufficient flexibility so as to be compressible by pressure exerted thereupon by the organ within which the catheter is inserted. The wall may have an opening wherein the discrete sensing area of the wall may be a flexible sleeve sealingly secured to the body and covering the opening.

The catheter further comprises at least one sensing optical fiber disposed within the lumen, the optical fiber extending from the proximal end wherein the fiber is connectable to both a device for providing a light input and a device for receiving a light signal from the optical fiber. The optical fiber further comprises a sensing segment adjacent the discrete sensing area of the wall. The sensing segment is deformable in response to compression of the discrete sensing area of the wall, whereby the light signal is attenuated. The catheter may further comprise a reference optical fiber disposed within the lumen of the body for use as a comparator with the sensing optical fiber.

The catheter may further comprise a positioning assembly disposed within the lumen adjacent the discrete sensing area of the wall (adjacent the opening and covered by the flexible sleeve in embodiments having a wall with an opening covered by a flexible sleeve) for positioning the sensing segment of the sensing optical fiber in a sensing position. The catheter may comprise more than one sensing segment adjacent a particular discrete sensing area and further may comprise more than one discrete sensing area on a single catheter.

DESCRIPTION OF THE PREFERRED EMBODIMENTS

The optical fiber pressure sensing catheter embodied in the present invention has several advantages: it has (1) electroisolation; (2) circumferential pressure measurement capabilities; (3) sphincter measurement capabilities; (4) more pressure measurement points; and (5) it does not require the patient to lie supine or hold the esophagus level.

Electro-isolation is important because of patient safety and cardiac artifact. Cardiac artifact is a result of electrical stimulation of the heart muscle being picked up by the electrical leads to and from the solid state transducer, or pressure being applied by the heart beating on the esophageal wall. This artifact is very difficult to distinguish from actual pressure signals.

Circumferential pressure measurements can be more easily made using the optical fiber catheter due to the small size of the fiber used in the catheter. The fiber size is important because it allows many pressure measurements to be made within a small area (smaller than the two previously mentioned probes) because several fibers can be housed in an equivalent size catheter. This capability enables the user to monitor esophageal pressure cross-sections and lessen the need for accurate positioning of the probe in the esophagus.

The lower esophageal sphincter (LES) is the muscle at the distal end of the esophagus that prevents stomach acids and secretions from re-entering the esophageal lumen. An accurate measurement of the LES diameter can be useful in diagnosing some esophageal disorders. The ability to make this measurement has been incorporated into the optical fiber catheter by stair stepping the sensing points near the distal tip of the probe. The sensing points (zones) would appear as a helical pattern on the catheter exterior. This design can, like the previously mentioned circumferential design, be used to accurately position the probe in the esophagus.

Due to the small fiber diameter, several fibers can be housed within the catheter tubing. This makes it possible to measure pressures circumferentially and longitudinally at a number of sites along the catheter. This will eliminate the need for a statistical reconstruction of the esophageal response.

Since the optical fiber probe does not require the use of any fluids to deduce pressure readings, the need to keep the esophagus level is eliminated. A reference fiber can be used to subtract out any unwanted noise artifacts due to movement. Use of the reference fiber allows the patient to sit or recline while the motility study is being performed.

The optical fiber pressure sensing catheter combines the best attributes of both the water perfused catheter and the solid state transducer catheter. For example, it allows more pressure measurement points without holding the esophagus level. Also, due to the simple design, it can be constructed less expensively than the other two mentioned catheters. These advantages should greatly enhance the capabilities and make esophageal motility studies more affordable to the patient.

Experimental Procedures

The process of building an optical fiber esophageal catheter presented many problems. The first step was to define a procedure to test potential fiber candidates.

This test measured fiber sensitivity to pressure by relating pressure to the drop in optical power due to microbend losses.

Pressure Chamber

One meter of fiber under examination was terminated and mounted in connectors in order to make the appropriate attachments to the source and detection devices. One end of the terminated fiber was connected to a light source (light emitting diode, LED) while the other end was connected to a detector (PIN diode). Each end of the fiber sample was held in a bushing and polished to an acceptable level. The terminated fiber ends were mated to the LED and the PIN diode through the use of threaded connectors. Both the LED and the PIN diode were mounted in a threaded bushing. This mounting was done by the supplying vendor and entailed holding the LED and the PIN diode in a jig having x-y positioners. The active devices were moved until maximum optical power was coupled or detected by butting a 200 micron step-index silica fiber to the source or a detector. Then, the devices were secured in the threaded bushing and potted for use.

Light was coupled into the fiber by the LED and detected by the PIN photodiode. The fiber was held straight by securing the fiber to a wooden dowel rod. On the dowel rod was placed a bead or ridge that was 0.5 mm in diameter and raised 0.5 mm above the wooden dowel rod surface. The ridge was the only perturbation in the straight fiber sample. The fiber sample was shielded entirely except at the microbend ridge where it was exposed to pressure. The mounted fiber was placed in a pressure chamber in order to apply pressure on the fiber at the microbend ridge. This pressure caused the fiber to conform to the ridge and induce optical power loss.

The pressure chamber used in these fiber tests was designed to simulate an esophageal contraction. The pressure chamber consisted of two glass tubes one approximately 0.5 inches ID and the other 2.0 inches OD, two rubber stoppers, a rubber bladder, and a support frame.

The two rubber stoppers were large enough to completely seal the ends of the 2.0 inch glass tube. In each rubber stopper a hole was cut to accept the 0.5 inch glass tube. In addition in one stopper, a hole was cut to accept a glass elbow. This elbow was connected to an air bulb which was used to pump air into the chamber. Also, in line was a pneumatic gauge to measure pressure in the chamber. Approximately 0.5 inches of the glass tube was replaced by a rubber bladder. This 0.5 inch portion of bladder was placed in the middle of the 0.5 inch diameter glass tube. The 0.5 inch tube with the bladder in place was mounted in the rubber stoppers and inserted in the 2.0 inch tube, and then placed in a supporting structure. The fiber to be tested, mounted on the dowel rod, was inserted in the 0.5 inch tubing and the bend-ridge was positioned in the middle of the rubber bladder and secured. As air was pumped into the chamber the rubber bladder collapsed and forced the fiber to conform to the bend-ridge which induced optical power losses due to mode coupling. This rubber bladder collapsed around the dowel rod and fiber, but was not trapped between the fiber and dowel rod. This closely simulated an esophageal contraction found in the human body. From this, an accurate relation between pressure and optical power loss could be determined and a mathematical relationship established.

Optical Fiber Testing

It was determined that currently available plastic fibers could not be used in this particular sensing application because of permanent inelastic deformation of the fiber. The environment and catheter construction also prevented the replacement of the damaged plastic fiber. Therefore, the investigation into which fiber material and fiber size to use was devoted to glass fibers only.

Several silica fibers were tested and compared. It was observed that if the fiber diameter exceeded 200 microns, the fiber did not achieve the sensitivity needed for the low pressures required in this application. Since optical fibers were shielded with protective jackets to protect against microbend losses a balance between strength and sensitivity had to be established. The appropriate jacket material had to be determined to establish this balance. In order to place a sufficient number of fibers in the catheter, and increase capabilities, smaller fiber diameters were used. In the considered design, the fiber had to be able to make an acute bend at the distal tip of the catheter. This bend (approximately 2 mm in radius) was needed to return the signal to the detector. This distal bend, could not reduce the detected optical power by more than 50 percent or the sensitivity would be insufficient to detect pressures between 0 and 240 mmHg.

After testing fibers that met these specifications a 100 micron silica fiber with a acrylic jacket was selected for further experimentation.

Using the chosen fiber, pressures were measured over a range of between 0–240 mmHg. As a result, all esophageal disorders could be diagnosed within this pressure range. The high end of the pressure range would be useful mainly to diagnose nutcracker esophagus while the lower end could be useful to analyze presbyesophagus.

Catheter Tubing

The catheter tubing had to be of sufficient flaccidity (flexibility) to bend around the nasal cavity upon insertion but of sufficient rigidity not to kink. An aliphatic polyurethane-based material was selected. The outside diameter, of the tubing was approximately 5 mm and had a durometer reading of approximately 100 shore. This tubing provided sufficient protection against unwanted microbends and was sufficiently large to house a number of sensing fibers. The tubing material was doped with barium sulfate to cause the catheter to be x-ray opaque. This could be helpful by allowing other tests to be performed simultaneously without requiring the catheter to be removed.

At some point in the traversal of the fiber through the catheter system, the fiber or fibers would be exposed to the esophageal pressures. This necessitated the design of a sensing shield which would house and shield all fibers except the particular one used for sensing in the particular area. After much experimentation, a brass ferrule of approximately 8–9mm in length and 4 mm in diameter was constructed. The sensing ferrule had a ridge placed on the outside, in the middle of the ferrule, and a groove cut in the ferule to hold stable the sensing fiber. This ferrule design did not constrict the bending of the sensing fiber. The ridge was orthogonal to the longitudinal axis of the sensing fiber. The ridge had the same dimensions as the ridge used in the fiber testing procedure described. Each end of the sensing ferrules fit tightly into the ends of the catheter tubing and each end was secured by glue. The length of the sensing ferrule was, by design, forced to be approximately 5-9 mm in order to insure that the catheter would be flexible enough to be bent during intubation.

The use of a reference fiber to remove unwanted noise and to take into account any losses due to intubation was also investigated especially for the purpose of ambulatory studies. This reference fiber traversed the catheter and was never exposed to esophageal pressures. The only losses incurred by this fiber were expected to be due to the bends in placement of the catheter. For example, all fibers would be bent around the nasal cavity so this loss could be accounted for by using the reference fiber. This technique isolated the bending losses to the sensing points and allowed all other extraneous losses to be subtracted. Because of the distal bend at the catheter tip, the fibers were fragile and easily broken necessitating extra protection at the distal tip. The fiber studied had a critical bend radius, (the radius at which the fiber breaks), of 3 mm. First each fiber was bent around a mandrel having approximately a 4 mm diameter and glued. This mandrel prevented the fiber from collapsing due to external pressure applied to the bend. The distal tip was sealed with a cap of the same material as the catheter tubing. This cap was secured to the end of the catheter by glue.

Each sensing zone was sealed. A rubber (latex) bladder (sleeve) was placed over each sensing zone and was secured with glue thereby sealing the sensing zone. This sleeve did not restrict the bending of the sensing fiber nor was it trapped between the fiber and sensing sleeve. The zone was also coated with a medical grade sealant to ensure a good seal. This sealing technique described did not significantly reduce the sensitivity of the probe in comparison to a bare optical fiber.

All components were obtained from commercial sources. Optical fibers were model number 16-100S obtained from General Fiber Optics. The all silica multi-mode step-index fibers were 100/140 (core/cladding) microns in diameter. They had a core refractive index of 1.468, a cladding refractive index of 1.4, and a numerical aperture of 0.24. The tubing, from Thermedics, Inc., was composed of an aliphatic thermoplastic polyurethane having a 0.130 inch internal diameter and a 0.177 inch external diameter. The tubing had a hardness of 100A Shore and was radiopaque. Light emitting diodes from General Fiber Optics had a peak output at 850 nm, were AMP mounted and were part number 80-0850-1002. PIN diodes/photodetectors from General Fiber Optics had a peak sensitivity at 850 nm, had AMP mountings, and were part number 81-0850-1001, both from General Fiber Optics. The laser diode was part number LT020MC0 obtained from Sharp. The bidirectional coupler was obtained from General Fiber Optics. The computer and software was DAS-16G1 and Metrabyte/Asyst/DAC from Keithley-Metrabyte. The glue for sealing the ferrule to the tubular housing was model 890 from Dow Corning. All components described above are representative of materials available through commercial sources used to construct the preferred embodiments of the invention described herein.

First Preferred Embodiment

Figure 1:
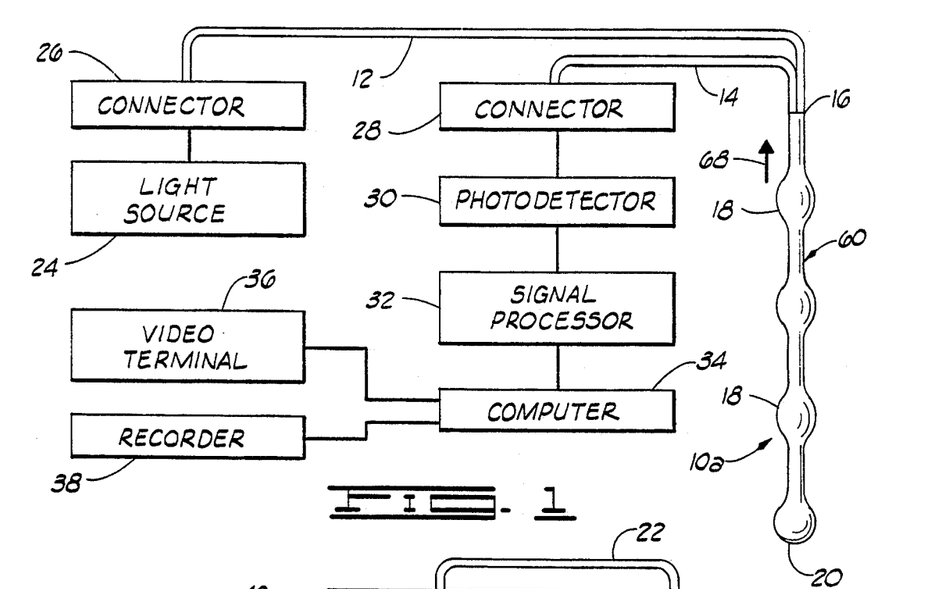
FIG. 1 is a schematic of an optical fiber pressure sensing catheter system having separate optical fiber input and output.

In the preferred embodiment, the present invention is an optical fiber pressure sensing catheter 10a (FIG. 1). The catheter 10a is designed in particular for use in measuring motility in an esophagus but may be used within other organs of the alimentary and gastrointestinal tract such as the small intestine and colon, and it may be used within the venous and arterial systems of a mammal to detect intravascular pressures.

Figure 3:
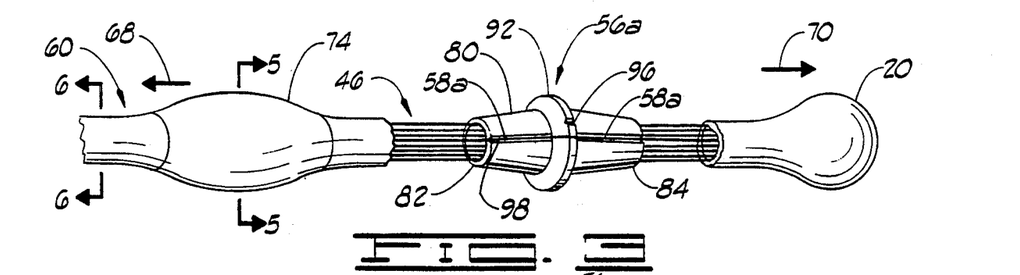
FIG. 3 is a perspective view of a portion of an optical fiber sensing catheter revealing the positioning assembly and optical fiber assembly.

The catheter 10a houses an optical fiber assembly 46 (FIG. 3) having at least one optical fiber, the assembly 46 having an input end 12 and an output end 14. The catheter 10a has a first end 16 and a second end 20 and at least one sensing zone 18 which may appear as a slight bulge in the catheter 10a (FIG. 1). In the preferred embodiment, a device for providing a light input 24 such as a light-emitting diode, is attached to the input end 12 of the catheter 10a via a connector 26 for passing a light signal through the optical fiber assembly 46.

A device for receiving a light signal, such as a photodetector 30, is connected via a connector 28 to the output end 14 of the optical fiber assembly 46 of the catheter 10a for measuring the power of the light signal passing through the optical fiber assembly 46 and for emitting an electrical signal to a signal processor 32 for converting the signal into a pressure reading. An amplifying apparatus (not shown) may be connected to the photodetector 30 for amplifying the electrical signals from the photodetector 30. Alternatively, the amplifying apparatus may be a component of software used to drive a computer 34 connected to the signal processor 32. A signal filtering apparatus (not shown) may also be connected to the signal processor 32 to improve the signal or may be a component of software. A video terminal 36 and a recorder 38 may be connected to the computer 34.

Figure 7A:
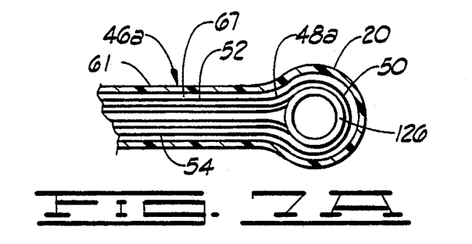
FIG. 7A is a side-sectional view through the distal end of a catheter having U-shaped optical fibers.

In the preferred embodiment, the optical fiber pressure sensing catheter 10a comprises an optical fiber assembly 46 which more particularly is a U-shaped optical fiber assembly 46a (FIG. 7A) comprised of at least one U-shaped sensing optical fiber 48a having a first end (not shown) which is connectable to connector 26 and a second end (not shown) which is connectable to connector 28 and a bend 50 (FIG. 7A). A first arm 52 of the U-shaped optical fiber 48a extends from the first end to the bend 50 and a second arm 54 of the U-shaped sensing optical fiber 48a extends from the second end to the bend 50. The first arm 52 and the second arm 54 are aligned generally parallel to each another. The catheter 10a may also have a U-shaped reference optical fiber (not shown) substantially similar in shape and composition to the U-shaped sensing optical fiber 48a, wherein the U-shaped reference optical fiber (not shown) also has a first end, a second end and a bend wherein a first arm extends from the first end to the bend and a second arm extends from the second end to the bend, the first arm and the second arm aligned generally parallel to one another.

The catheter 10a of the preferred embodiment is further comprised of a flexible body 60 (FIGS. 3 an 4) having a wall 61, a closed proximal end 16, a closed distal end 20, an internal diameter 64, an external diameter 66, and a lumen 67 (FIGS. 6-7B) between the proximal end 16 and the distal end 20. The first arm 52 and the second arm 54 of the sensing optical fiber 48a and the first arm and the second arm of the reference optical fiber (not shown), if present, are disposed generally parallel to one another within the lumen 67 of the body 60 such that the first arm 52 and the second arm 54 of the sensing optical fiber 48a and the first arm and the second arm of the reference optical fiber (not shown), if present, both extend in the direction 68 (FIG. 3) toward the proximal end 16 of the body 60 and the bend 50 of the sensing optical fiber 48a and the bend of the reference optical fiber (not shown) are disposed generally in the distal end 20 of the body 60.

Figure 4:
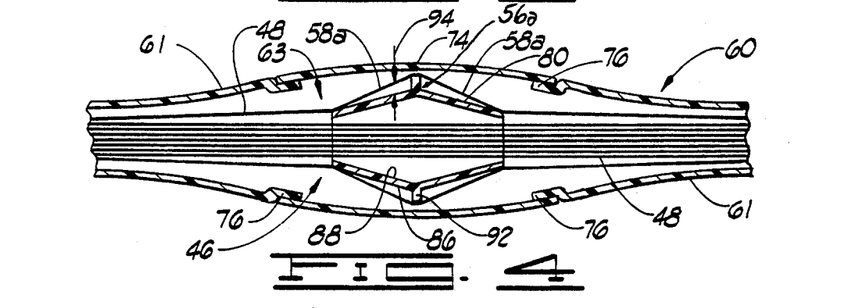
FIG. 4 is a side-sectional view through a sensing area.

The wall 61 of the body 60 of catheter 10a has at least one opening 63 (FIG. 4) between the proximal end 16 and the distal end 20. A positioning assembly and a sensing segment are disposed within the lumen adjacent the opening 63. A discrete sensing area, which in the preferred embodiment is a flexible sleeve 74, is comprised of a thin latex film, and is disposed over the positioning assembly, the sensing segment, and the opening 63 for covering the opening 63, the positioning assembly and the sensing segment wherein is formed the sensing zone 18. Each end of the flexible sleeve 74 is sealingly secured to a securing position on the wall 61 around the opening 63, which may be a securing lip 76 (FIG. 4). When sufficient pressure is applied by the organ (not shown) against the sleeve 74, the sensing segment is caused to be deformed thereby causing an attenuation in the power of a light signal passing through the sensing optical fiber 48a.

Figure 5:
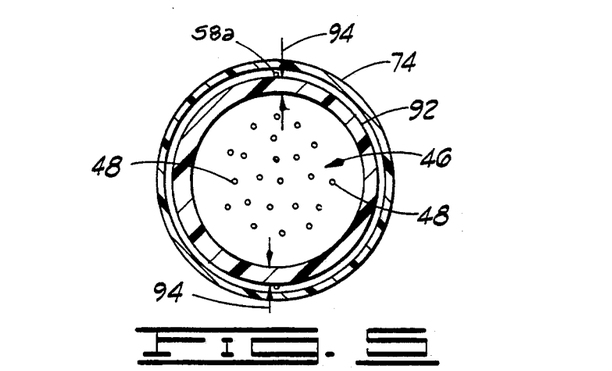
FIG. 5 is a cross-sectional view through the fulcrum of a ferrule-type positioning assembly bearing two optical fibers.
Figure 9:
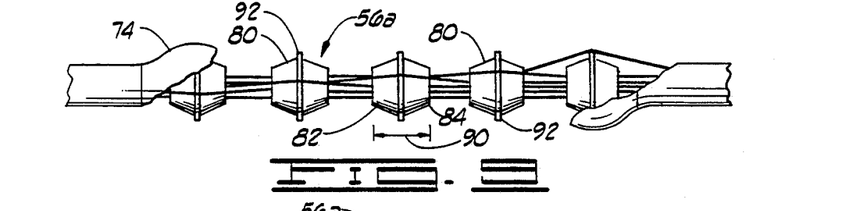
FIG. 9 is a perspective view of a catheter having a plurality of sensing zones having ferrule-type positioning assembly which have been exposed to view.
Figure 10:
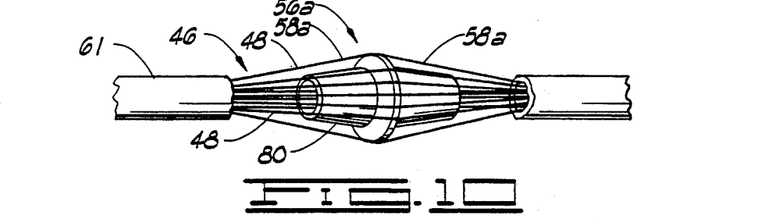
FIG. 10 is a perspective view of an embodiment in which the sensing zone comprises a plurality of optical fiber sensing segments.

In the preferred embodiment, the positioning assembly of the catheter 10a further comprises a ferrule-type positioning assembly 56a (FIGS. 3, 4, 9, 10) having a ferrule 80 (FIGS. 3 and 4) having a first end 82, a second end 84, an external surface 86, an internal surface 88, and a longitudinal axis 90 (FIG. 9) extending from the first end 82 to the second end 84. Further, the ferrule-type positioning assembly 56a comprises an annular fulcrum 92 positioned externally along the midline of the circumference of the external surface 86 of the ferrule 80. The sensing segment, further defined as a sensing segment 58a (FIGS. 3, 4, 9, 10) comprises the portion of the U-shaped sensing optical fiber 48a which is positioned in the sensing position by the positioning assembly 56a. The sensing position (FIGS. 3 and 4) is further described as being the position of the sensing segment 58a wherein the sensing segment 58a is disposed outside the ferrule 80 in an orientation parallel to the longitudinal axis 90 (FIG. 9) of the ferrule 80 and is supported by the fulcrum 92 of the ferrule 80. The fulcrum 92 thereby serves to position the sensing segment 58a a distance 94 (FIGS. 4 and 5) beyond the external surface 86 of the ferrule 80. Furthermore, the ferrule 80 has a stabilizer for holding the sensing optical fiber 48a stable thereagainst. The stabilizer may be either a nick 96 in the fulcrum 92, or in the preferred embodiment, a groove 98 in the ferrule 80 wherein a portion of the sensing segment 58a lays in the groove 98.

Figure 13A:
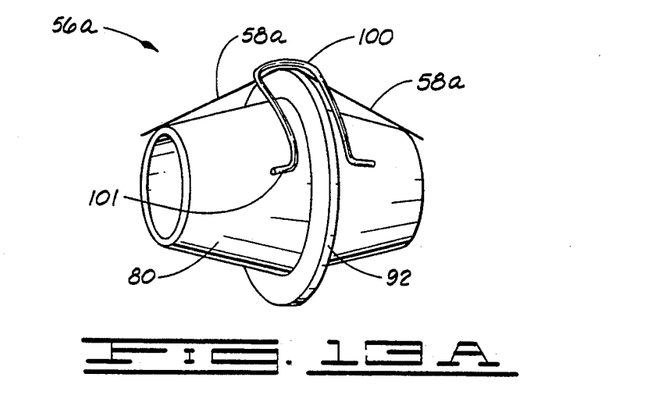
FIG. 13A is a perspective view of a ferrule-type positioning assembly having a depressing device.
Figure 13B:
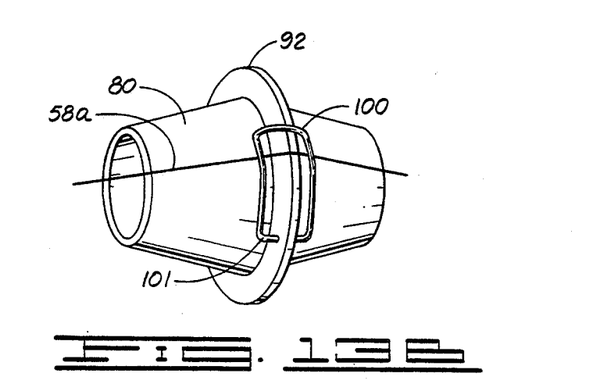
FIG. 13B is another view of the positioning assembly of FIG. 13A.
Figure 13C:
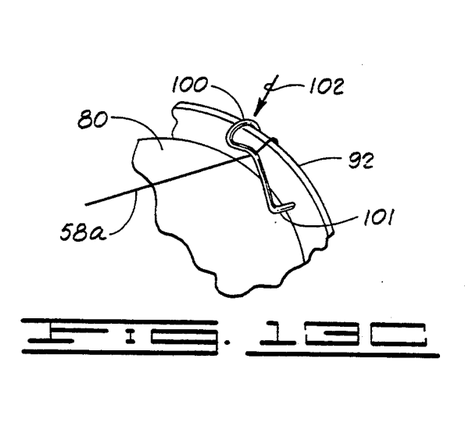
FIG. 13C is a view of the positioning assembly of FIG. 13B with the depressing device compressing the sensing segment of the sensing optical fiber.
Figure 13D:
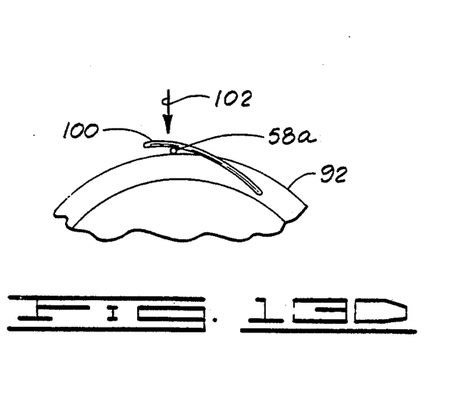
FIG. 13D is a side view of the positioning assembly of FIG. 13B.

In the preferred embodiment, the positioning assembly 56a further comprises a depressing device illustrated in FIGS. 13A–13D as a clip 100. The clip 100 is hingeably attached by a hinge end 101 to the ferrule 80 (FIG. 13A) or to the fulcrum 92 (FIGS. 13B–C) of the positioning assembly 56a. The clip 100 rests against the sensing segment 58a and beneath the flexible sleeve 74. When pressure is applied against the discrete sensing area (in this case the flexible sleeve 74), the clip 100 is depressed in direction 102 wherein the sensing segment 58a is deformed (FIG. 13C). The clip 100 thereby serves to accentuate the deforming effect of the flexible sleeve 74 upon the sensing segment 58a when the flexible sleeve 74 is compressed.

Figure 11:
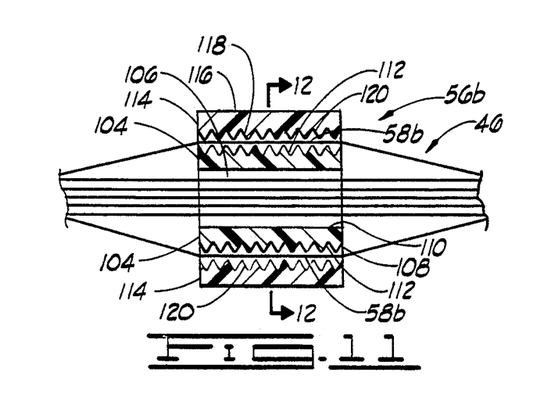
FIG. 11 is a side-sectional view of a ring-type positioning assembly.
Figure 12:
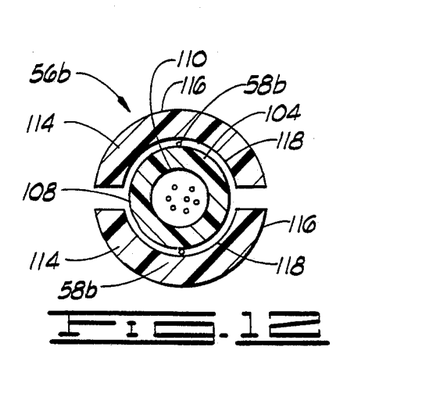
FIG. 12 is a cross-sectional view of a ring-type positioning assembly.

Alternatively, the positioning assembly comprises a ring-type positioning assembly 56b (FIGS. 11 and 12) which is comprised of an inner ring 104 having a longitudinal bore 106 extending longitudinally therethrough and at least one outer plate 114. The inner ring 104 can be further defined as having an exterior surface 108 having at least one corrugation 112 and an interior surface 110 (FIGS. 11 and 12). The outer plate 114 is shown in FIG. 12 as curved but it may have other shapes as well which are adapted to the shape in the inner ring 104.

The outer plate 114 has an exterior surface 116 and an interior surface 118, the interior surface 118 further comprising at least one corrugation 120 meshable with the corrugation 112 of the inner ring 104. The outer plate 114 is positioned adjacent the inner ring 104 wherein the interior surface 118 of the outer plate 120 is near the exterior surface 108 of the inner ring 104.

The sensing position of the sensing optical fiber 48a in the ring-type positioning assembly 56b (FIGS. 11 and 12) is further described as being the position of the sensing segment 58b wherein the sensing segment 58b is sandwiched between the corrugation 112 of the inner ring 104 and the corrugation 120 of the outer plate 114 wherein when the outer plate 114 is pressed toward the exterior surface 108 of the inner ring 104, the sensing segment 58b is deformed between the corrugation 120 of the outer plate 114 and the corrugation 112 of the inner ring 104.

Each catheter 10a has at least one sensing zone 18. Alternative embodiments of the catheter 10a have more than one sensing zone 18 (FIGS. 1, 3, 8–9). Each sensing zone 18 is comprised of one sensing segment 58a (FIGS. 3, 9) in the case of a ferrule-type positioning assembly 56a or one sensing segment 58b (not shown) in the case of a ring-type positioning assembly. Alternatively, a sensing zone 18 may have two or more sensing segments 58a (FIGS. 4–5, 10) in the case of a ferrule-type positioning assembly 56a or two or more sensing segments 58b (FIGS. 11–12) in the case of a ring-type positioning assembly 56b.

The catheter 10a is connectable to a light source 24 connected via a connector 26 to the input end 12 of the U-shaped optical fiber assembly 46a for passing a light signal therethrough. A photodetector 30 is connectable the output end 14 of the U-shaped optical fiber assembly 46a via the connector 28 for receiving the light signal and for emitting an electrical signal. An amplifying apparatus (not shown) may be connected to the photodetector (30) for amplifying the electrical signals from the photodetector 30. A signal filtering apparatus (not shown) may be connected to the amplifier for filtering the amplified electrical signal. And, a signal processor 32 connected to the photodetector 30 converting the signal into a pressure reading.

In the preferred embodiment, the catheter 10a may further comprise a rigid mandrel 126 (FIG. 7A) located in the distal end 20 of the body 60 around which the bend 50 in the U-shaped sensing optical fiber 48a and the bend in the reference optical fiber (not shown) are formed and to which the sensing fiber bend 50 and the reference fiber bend (not shown) are secured, for example by a glue, for providing support and strength to the sensing fiber bend 50 and the reference fiber bend (not shown).

In the preferred embodiment, the optical fiber assembly 46 of the catheter 10a comprises optical fibers 48a having cross-sectional diameters less than or equal to about 200 micrometers. More particularly, the optical fibers 48a have cross-sectional diameters in a range from about 30 micrometers to about 150 micrometers. The body 60 may have an external diameter of up to about 7 millimeters, or more particularly, an external diameter in the range of from about three to about six millimeters. Additionally, in the preferred embodiment, the body 60 is doped with a material such as barium sulfate for making the wall 61 radiopaque.

Second Preferred Embodiment

Figure 2:
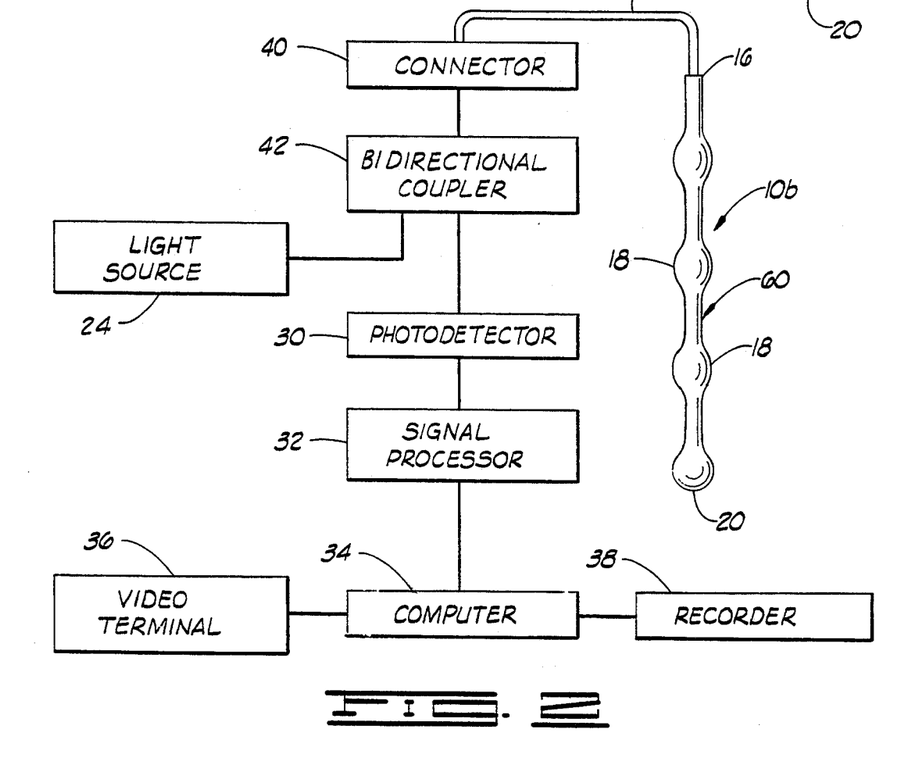
FIG. 2 is a schematic of an optical fiber pressure sensing catheter system having bidirectional input/output.

In an alternate preferred embodiment, the present invention is an optical fiber pressure sensing catheter 10b (FIG. 2). The catheter 10b, like the catheter 10a, is designed in particular for use in measuring intraesophageal motility but may be modified to be used in other organs of the alimentary tract such as the small intestine and colon, and it may be modified to detect intravascular pressures in the venous and arterial systems of a mammal.

The catheter 10b houses an optical fiber assembly 46 (FIG. 3) having a combined input/output end 22 (FIG. 2). The catheter 10b has a first end 16 and a second end 20 and at least one sensing zone 18. A light source 24 is attached to the input/output end 22 of the catheter 10b via a bidirectional coupler 42 which in turn is connected to a connector 40 for passing a light signal through the optical fiber assembly 46.

A photodetector 30 is connected to the bidirectional coupler 42 for measuring the power of the optical signal passing through the optical fiber assembly 46 and for emitting an electrical signal to a signal processor 32 for converting the signal into a pressure reading. An amplifying apparatus (not shown) may be connected to the photodetector 30 for amplifying the electrical signals from the photodetector 30.

Alternatively, the amplifying apparatus may be a component of software used to drive a computer 34 connected to the signal processor 32. A signal filtering device (not shown) may also be connected to the signal processor 32 to improve the signal or may be a component of software. A video terminal 36 and a recorder 38 may be connected to the computer 34.

Figure 7B:
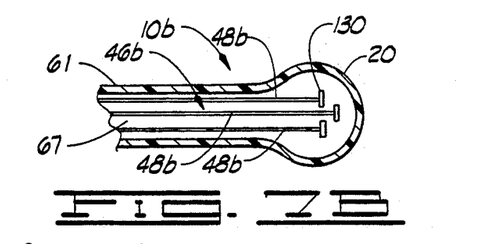
FIG. 7B is a side-sectional view through the distal end of a catheter having linear optical fibers.
Figure 8:
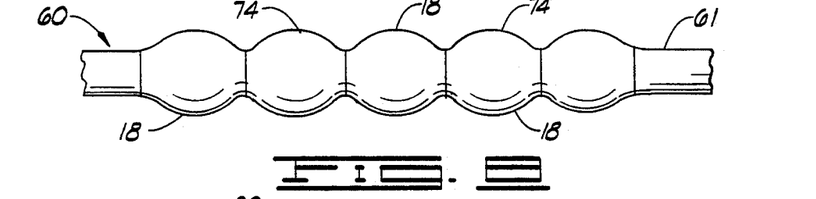
FIG. 8 is a perspective view of a catheter having a plurality of sensing zones.

In this embodiment, the optical fiber pressure sensing catheter 10b comprises an optical fiber assembly 46 which more particularly is a linear optical fiber assembly 46b (FIG. 7B) comprised of at least one linear sensing optical fiber 48b having a first end (not shown) which is connectable to connector 40 and a mirrored end 130 which is disposed in or near the distal end 20 of the catheter 10b (FIG. 7B). The catheter 10b may also have a linear reference optical fiber (not shown) substantially similar in shape and composition to the linear sensing optical fiber 48b, wherein the linear reference optical fiber (not shown), if present, has a first end and a mirrored end.

Figure 6:
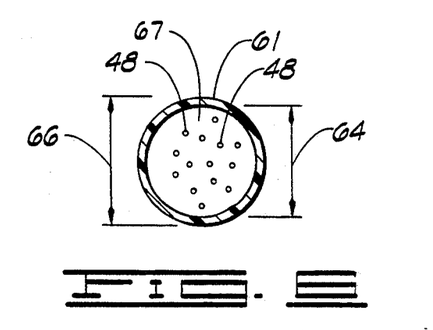
FIG. 6 is a cross-sectional view through a portion of the tubular housing showing a plurality of optical fibers.

The catheter 10b of this embodiment is further comprised of a flexible body 60 (FIGS. 3 and 4) having a wall 61, a proximal end 16, a distal end 20, an internal diameter 64 and an external diameter 66 (FIG. 6). The linear sensing optical fiber 48b and the reference optical fiber (not shown), if present, are disposed generally parallel to one another within the tubular housing 62 such that the first end (not shown) of the linear sensing optical fiber 48b and the first end of the reference optical fiber (not shown) both extend in the direction 68 (FIG. 3) toward the connector 40 and the mirrored end 130 of the linear sensing optical fiber 48b and the mirrored end of the reference optical fiber (not shown) are disposed generally in the distal end 20 of the body 60.

The wall 61 of the body 60 of catheter 10b has at least one opening 63 (FIG. 4) between the proximal end 16 and the distal end 20. A positioning assembly and a sensing segment are disposed within the lumen adjacent the opening 63. A discrete sensing area, which in the preferred embodiment is a flexible sleeve 74, is comprised of a thin latex film, and is disposed over the positioning assembly, the sensing segment, and the opening 63 for covering the opening 63, the positioning assembly and the sensing segment wherein is formed the sensing zone 18. Each end of the flexible sleeve 74 is sealingly secured to a securing position on the wall 61 around the opening 63, which may be a securing lip 76 (FIG. 4). When sufficient pressure is applied by the organ (not shown) against the sleeve 74, the sensing segment is caused to be deformed thereby causing an attenuation in the power of a light signal passing through the sensing optical fiber 48a.

In the preferred version of this embodiment, the positioning assembly of the catheter 10b further comprises a ferrule-type positioning assembly 56a (FIGS. 3, 4, 9, 10) having a ferrule 80 (FIGS. 3 and 4) having a first end 82, a second end 84, an external surface 86, an internal surface 88, and a longitudinal axis 90 (FIG. 9) extending from the first end 82 to the second end 84. Further, the ferrule-type positioning assembly 56a comprises an annular fulcrum 92 positioned externally along the midline of the circumference of the external surface 86 of the ferrule 80. A sensing segment 58a (FIGS. 3, 4, 9, 10) comprises the portion of the linear sensing optical fiber 48b which is positioned in the sensing position by the positioning assembly 56a. The sensing position (FIGS. 3 and 4) is further defined as being the position of the sensing segment 58a wherein the sensing segment 58a is disposed outside the ferrule 80 in an orientation parallel to the longitudinal axis 90 (FIG. 9) of the ferrule 80 and is supported by the fulcrum 92 of the ferrule 80. The fulcrum 92 thereby serves to position the sensing segment 58a a distance 94 (FIGS. 4 and 5) beyond the external surface 86 of the ferrule 80. Furthermore, the ferrule 80 has a stabilizer for holding the sensing optical fiber 48b stable thereagainst. The stabilizer may be either a nick 96 in the fulcrum 92, or in the preferred version of this embodiment, a groove 98 in the ferrule 80 wherein a portion of the sensing segment 48b lays in the groove 98. In the preferred embodiment, as described previously, the positioning assembly 56a comprises a depressing device 100 for depressing the sensing segment 58a, as indicated in FIGS. 13A-D.

In an alternative version of this embodiment, the positioning assembly further comprises a ring-type positioning assembly 56b (FIGS. 11 and 12) which is comprised of an inner ring 104 having a longitudinal bore 106 extending longitudinally therethrough and at least one outer plate 114. The inner ring 104 can be further defined as having an exterior surface 108 having at least one corrugation 112 and an interior surface 110 (FIGS. 11 and 12). The outer plate 114 is shown in FIG. 12 as curved but it may have other shapes as well which are adapted to the shape in the inner ring 104.

The outer plate 114 has an exterior surface 116 and an interior surface 118, the interior surface 118 further comprising at least one corrugation 120 meshable with the corrugation 112 of the inner ring 104. The outer plate 114 is positioned adjacent the inner ring 104 wherein the interior surface 118 of the outer plate 120 is near the exterior surface 108 of the inner ring 104.

The sensing position of the linear sensing optical fiber 48b in the ring-type positioning assembly 56b (FIGS. 11 and 12) is further described as being the position of the sensing segment 58b wherein the sensing segment 58b of the linear sensing optical fiber 48b is sandwiched between the corrugation 112 of the inner ring 104 and the corrugation 120 of the outer plate 114 wherein when the outer plate 114 is pressed toward the exterior surface 108 of the inner ring 104, the sensing segment 58b is deformed between the corrugation 120 of the outer plate 114 and the corrugation 112 of the inner ring 104. When pressure is relieved, the sensing segment 58b returns to its original form.

Each catheter 10b has at least one sensing zone 18. Alternative embodiments of the catheter 10b have more than one sensing zone 18 (FIGS. 2-3, 8-9). Each sensing zone 18 is comprised of one sensing segment 58a (FIGS. 3, 9) in the case of a ferrule-type positioning assembly 56a or one sensing segment 58b (not shown) in the case of a ring-type positioning assembly. Alternatively, a sensing zone 18 may have two or more sensing segments 58a (FIGS. 4-5, 10) in the case of a ferrule-type positioning assembly 56a or two or more sensing segments 58b (FIGS. 11-12) in the case of a ring-type positioning assembly 56b.

The catheter 10b is provided with a light source 24 connected via a bidirectional coupler 42 and a connector 40 to the input/output end 22 of the linear optical fiber assembly 46b for passing a light signal therethrough. A photodetector 30 is connected to the bidirectional coupler 42 for receiving the light signal from the linear sensing optical fiber 48b and for emitting an electrical signal. An amplifying apparatus (not shown) may be connected to the photodetector (30) for amplifying the electrical signals from the photodetector 30. A signal filtering device (not shown) may be connected to the amplifier for filtering the amplified electrical signal. And, a signal processor 32 connected to the photodetector 30 converting the signal into a pressure reading.

In the preferred embodiment, the optical fiber assembly 46 of the catheter 10b comprises optical fibers 48b having cross-sectional diameters less than or equal to about 200 micrometers. More particularly, the optical fibers 48b have cross-sectional diameters in a range from about 30 micrometers to about 150 micrometers. The body 60 may have an external diameter of up to about 7 millimeters, or more particularly, an external diameter in the range of from about three to about six millimeters. Additionally, in the preferred embodiment, the body 60 is doped with a material such as barium sulfate for making the wall 61 of the body 60 radiopaque.

Preferred Embodiment of the Method

In the preferred embodiment of the method of use of the optical fiber sensing catheter 10a or 10b, the catheter 10a or 10b is used to measure the motility of an esophagus. The method comprises the first step of inserting the optical fiber pressure sensing catheter 10a or 10b into the esophagus (not shown). As described above, the catheter 10a or 10b comprises an elongated hollow body 60, having a wall 61, a closed proximal end 16, a closed distal end 20, and a lumen 67 therebetween. The wall 61 is generally noncompressible by pressure exerted thereupon by the esophagus except for at least one discrete sensing area of the wall 61 having sufficient flexibility so as to be compressible by pressure exerted thereupon by the esophagus.

The catheter 10a or 10b has an optical fiber assembly 46 further comprising a sensing optical fiber 48 disposed within the lumen 67 of the body 60. The optical fiber 48 extends from the proximal end 16 wherein the fiber 48 is connected to both a light input 24 for passing a light signal through the optical fiber 48 and a photodetector 30 for receiving the light signal from the optical fiber 48. The optical fiber 48 further comprises a sensing segment 58a or 58b adjacent the discrete sensing area of the wall 61. The sensing segment 58a or 58b is deformable in response to a compression of the discrete sensing area of the wall 61 associated with contraction of the esophagus which thereby causes an attenuated light signal when the sensing segment 58a or 58b is deformed.

Following insertion of the catheter 10a or 10b into the esophagus, a light signal is passed through the sensing optical fiber 48 of the inserted catheter 10a or 10b via the means 24 for providing light input. The light signal, which is attenuated when the sensing segment 58a or 58b of the sensing optical fiber 48 is caused to be deformed due to compression by the esophagus, is detected by the photodetector 30 for receiving the light signal. The power of the signal is measured and converted into an electrical signal. Then the electrical signal is processed into a pressure reading.

The optical fiber assembly 46 of the catheter 10a or 10b may further comprise a reference optical fiber (not shown) for serving as a comparator to the sensing optical fiber 48. The catheter 10a or 10b may also be further defined as having a positioning assembly such as a ferrule-type positioning assembly 56a or a ring-type positioning assembly 56b for positioning the sensing segment 58a or 58b in a sensing position. Additionally the sensing optical fiber 48 and the reference optical fiber may be a U-shaped optical fiber 48a or a linear optical fiber 48b as described above.

In alternative embodiments, the method of use of the optical fiber pressure sensing catheter may involve the insertion of the catheter into other organs of the body such as other organs of the alimentary and gastrointestinal tract and the vessels of the venous and arterial systems of the cardiovascular system.

Changes may be made in the embodiments of the invention described herein or in parts of the elements of the embodiments described herein or in the steps or in the sequence of steps of the methods described herein without departing from the spirit and scope of the invention as defined in the following claims.

What is claimed is:

1. An optical fiber pressure sensing catheter for detecting a discrete pressure within an organ, the catheter comprising:

an elongated hollow body, comprising a wall, an internal diameter, an external diameter, a closed proximal end, a closed distal end, a lumen therebetween, an a discrete opening in the wall between the distal end and the proximal end, the wall generally noncompressible by pressure exerted thereupon by the organ within which the catheter is inserted;

a flexible sleeve encompassing the opening and sealingly secured to the body around the opening thereby sealing the opening, the flexible sleeve having sufficient flexibility so as to be compressible by pressure exerted thereupon by the organ within which the catheter is inserted;

a sensing optical fiber disposed within the lumen, the optical fiber extending from the proximal end wherein the fiber is connectable to both a means for providing a light input and a means for receiving a light signal from the optical fiber;

means for measuring pressure comprising a sensing portion of the sensing optical fiber, the sensing portion adjacent the flexible sleeve and deformable in response to compression of the flexible sleeve, whereby the light signal is attenuated; and a positioning means disposed within the lumen of the body adjacent the flexible sleeve for positioning the sensing portion of the sensing optical fiber in a sensing position, the positioning means further comprising:
  a ferrule having a first end, a second end, an external surface, an internal surface, and a longitudinal axis extending from the first end to the second end,
  an annular fulcrum positioned circumferentially on the midline of the length of the external surface of the ferrule, and
  a stabilizing means for stably holding the sensing optical fiber, and wherein the sensing portion is disposed adjacent the external surface of the ferrule in an orientation generally parallel to the longitudinal axis of the ferrule and supported by the fulcrum of the ferrule, the fulcrum serving to position the sensing portion a distance beyond the external surface of the ferrule.

2. The catheter of claim 1 wherein the sensing optical fiber further comprises a U-shaped optical fiber having a first arm and a second arm and having a bend generally near the middle of the optical fiber, the first arm and the second arm arranged generally parallel to one another within the lumen of the body, the bend resting at the distal end.

3. The catheter of claim 2 further comprising a rigid mandrel located in the distal end of the body and around which the bend in the sensing optical fiber is formed and to which the bend is secured for providing support and strength to the bend.

4. The catheter of claim 2 further comprising a U-shaped reference optical fiber disposed within the lumen of the body and having a first arm, a second arm, and a bend.

5. The catheter of claim 4 further comprising a rigid mandrel located in the distal end of the body and around which the bends in the sensing optical fiber and the reference optical fiber are formed and to which the bends are secured for providing support and strength to the bends.

6. The catheter of claim 1 further comprising an optical fiber having a cross-sectional diameter less than or equal to about 200 micrometers.

7. The catheter of claim 6 further comprising an optical fiber having a cross sectional diameter in a range from about 30 micrometers to about 150 micrometers.

8. The catheter of claim 1 wherein the body has an external diameter of up to about 7 millimeters.

9. The catheter of claim 8 wherein the body has an external diameter in the range of from about three to about six millimeters.

10. The catheter of claim 1 further comprising a body doped with a material for making the tubing opaque to X-rays.

11. The catheter of claim 1 wherein the stabilizing means further comprises a groove in the ferrule.

12. The catheter of claim 1 wherein the stabilizing means further comprises a nick in the fulcrum.

13. The catheter of claim 1 further comprising a depressing means disposed upon the positioning means generally near the sensing portion of the sensing optical fiber wherein when the flexible sleeve of the wall is compressed, the depressing means presses against the sensing portion.

14. An optical fiber pressure sensing catheter for detecting a discrete pressure within an organ, the catheter comprising:
  an elongated hollow body, comprising a wall, an internal diameter, an external diameter, a closed proximal end, a closed distal end, a lumen therebetween, and a discrete opening in the wall between the distal end and the proximal end, the wall generally noncompressible by pressure exerted thereupon by the organ within which the catheter is inserted;
  a flexible sleeve encompassing the opening and sealingly secured to the body around the opening thereby sealing the opening, the flexible sleeve having sufficient flexibility so as to be compressible by pressure exerted thereupon by the organ within which the catheter is inserted;
  a U-shaped sensing optical fiber having a first end, a second end and a bend wherein a first arm extends from the first end to the bend and a second arm extends from the second end to the bend, the first arm and the second arm disposed within the lumen and aligned generally parallel to each other within the lumen of the body, the fiber connectable to both a means for providing a light input and a means for receiving a light signal from the optical fiber;
  means for measuring pressure comprising a sensing portion of the sensing optical fiber, the sensing portion adjacent the flexible sleeve and deformable in response to compression of the flexible sleeve, whereby the light signal is attenuated;
  a positioning means disposed within the lumen of the body adjacent the flexible sleeve for positioning the sensing portion of the sensing optical fiber in a sensing position; and
  a U-shaped reference optical fiber having a first end, a second end and a bend wherein a first arm extends from the first end to the bend and a second arm extends from the second end to the bend, the first arm and the second arm aligned generally parallel to one another within the lumen of the body.

15. The catheter of claim 14 further comprising a rigid mandrel located in the distal end and around which the bends in the sensing optical fiber and the reference optical fiber are formed and to which the bends are secured for providing support and strength to the bends.

16. The catheter of claim 14 wherein the positioning means further comprises:
  a ferrule having a first end, a second end, an external surface, an internal surface, and a longitudinal axis extending from the first end to the second end;
  an annular fulcrum positioned circumferentially on the midline of the length of the external surface of the ferrule and wherein the sensing position further comprises the sensing portion disposed outside the ferrule in an orientation parallel to the longitudinal axis of the ferrule and supported by fulcrum of the ferrule, the fulcrum serving to position the sensing portion a distance beyond the external surface of the ferrule; and
  a stabilizing means for stably holding the sensing optical fiber.

17. The catheter of claim 16 wherein the stabilizing means further comprises a groove in the ferrule.

18. The catheter of claim 16 wherein the stabilizing means further comprises a nick in the fulcrum.

19. The catheter of claim 14 further comprising a depressing means disposed upon the positioning means generally near the sensing portion of the sensing optical fiber wherein when the flexible sleeve of the wall is compressed, the depressing means presses against the sensing portion.

20. The catheter of claim 14 further comprising a sensing optical fiber having a cross-sectional diameter less than or equal to about 200 micrometers.

21. The catheter of claim 20 further comprising a sensing optical fiber having a cross sectional diameter in a range from about 30 micrometers to about 150 micrometers.

22. The body of claim 14 further comprising an external diameter of up to about 7 millimeters.

23. The body of claim 22 further comprising an external diameter in the range of from about three to about six millimeters.

24. The catheter of claim 14 further comprising a body doped with a material for making the tubing opaque to X-rays.

25. The catheter of claim 14 wherein the positioning means further comprises:
  rigid support means having an external surface; and
  a fulcrum positioned on the external surface of the rigid support means and wherein the sensing position further comprises the sensing portion disposed outside the rigid support means and supported by the fulcrum for positioning the sensing portion a distance beyond the external surface of the rigid support means.

26. The catheter of claim 25 further comprising a groove in the rigid support means for stabilizing the optical fiber.

27. The catheter of claim 25 further comprising a nick in the fulcrum for stabilizing the optical fiber.

28. An optical fiber pressure sensing catheter for detecting a discrete pressure within an organ, the catheter comprising:
  an elongated hollow body, comprising a wall, an internal diameter, and external diameter, a closed proximal end, a closed distal end, and a lumen therebetween, the wall generally noncompressible by pressure exerted thereupon by the organ within which the catheter is inserted except for at least one discrete sensing area of the wall having sufficient flexibility so as to be compressible by pressure exerted thereupon by the organ within which the catheter is inserted;
  a U-shaped sensing optical fiber disposed within the lumen, the optical fiber extending from the proximal end wherein the fiber is connectable to both a means for providing a light input and a means for receiving a light signal from the optical fiber, the optical fiber further comprising a first arm and a second arm and having a bend generally near the middle of the optical fiber, the first arm and the second arm arranged generally parallel to one another within the body, the bend resting at the distal end;
  means for measuring pressure comprising a sensing portion of the sensing optical fiber, the sensing portion adjacent each of the at least one discrete sensing areas of the wall and deformable in response to compression of the discrete sensing area of the wall, whereby the light signal is attenuated; and
  a positioning means disposed within the lumen adjacent the discrete sensing area of the wall for positioning the sensing portion of the sensing optical fiber in a sensing position.

29. The catheter of claim 28 further comprising a rigid mandrel located in the distal end and around which the bend in the sensing optical fiber is formed and to which the bend is secured for providing support and strength to the bend.

30. The catheter of claim 28 further comprising a U-shaped reference optical fiber disposed within the lumen of the body and having a first arm, a second arm, and a bend.

31. The catheter of claim 30 further comprising a rigid mandrel located in the distal end and around which the bends in the sensing optical fiber and the reference optical fiber are formed and to which the bends are secured for providing support and strength to the bends.

32. The catheter of claim 28 wherein the positioning means further comprises:
  a ferrule having a first end, a second end, an external surface, an internal surface, and a longitudinal axis extending from the first end to the second end;
  an annular fulcrum positioned circumferentially on the midline of the length of the external surface of the ferrule and wherein the sensing position further comprises the sensing portion disposed outside the ferrule in an orientation parallel to the longitudinal axis of the ferrule and supported by the fulcrum of the ferrule, the fulcrum serving to position the sensing portion a distance beyond the external surface of the ferrule; and
  a stabilizing means for stably holding the sensing optical fiber.

33. The catheter of claim 32 wherein the stabilizing means further comprises a groove in the ferrule.

34. The catheter of claim 32 wherein the stabilizing means further comprises a nick in the fulcrum.

35. The catheter of claim 32 further comprising a depressing means disposed upon the positioning means generally near the sensing portion of the sensing optical fiber wherein when the discrete sensing area of the wall is compressed, the depressing means presses against the sensing portion.

36. The catheter of claim 28 wherein the positioning means further comprises:
  rigid support means having an external surface; and
  a fulcrum positioned on the external surface of the rigid support means and wherein the sensing position further comprises the sensing portion disposed outside the rigid support means and supported by the fulcrum for positioning the sensing portion a distance beyond the external surface of the rigid support means.

37. The catheter of claim 36 further comprising a groove in the rigid support means for stabilizing the optical fiber.

38. The catheter of claim 36 further comprising a nick in the fulcrum for stabilizing the optical fiber.

39. An optical fiber pressure sensing catheter for detecting a discrete pressure within an organ, the catheter comprising:
  an elongated hollow body, comprising a wall, and internal diameter, an external diameter, a closed proximal end, a closed distal end, a lumen therebetween, and a discrete opening in the wall between the distal end and the proximal end, the wall generally noncompressible by pressure exerted thereupon by the organ within which the catheter is inserted;

a flexible sleeve encompassing the opening and sealingly secured to the body around the opening thereby sealing the opening, the flexible sleeve having sufficient flexibility so as to be compressible by pressure exerted thereupon by the organ within which the catheter is inserted;

a U-shaped sensing optical fiber disposed within the lumen, the optical fiber extending from the proximal end wherein the fiber is connectable to both a means for providing a light input and a means for receiving a light signal from the optical fiber, the optical fiber further comprising a first arm and a second arm and having a bend generally near the middle of the optical fiber, the first arm and the second arm arranged generally parallel to one another within the body, the bend resting at the distal end;

means for measuring pressure comprising a sensing portion of the sensing optical fiber, the sensing portion adjacent the flexible sleeve, and deformable in response to compression of the flexible sleeve, whereby the light signal is attenuated; and a positioning means disposed within the lumen of the body adjacent the flexible sleeve for positioning the sensing portion of the sensing optical fiber in a sensing position.

40. The catheter of claim 39 further comprising a rigid mandrel located in the distal end and around which the bend in the sensing optical fiber is formed and to which the bend is secured for providing support and strength to the bend.

41. The catheter of claim 39 further comprising a U-shaped reference optical fiber disposed within the lumen of the body and having a first arm, a second arm, and a bend.

42. The catheter of claim 41 further comprising a rigid mandrel located in the distal end and around which the bends in the sensing optical fiber and the reference optical fiber are formed and to which the bends are secured for providing support and strength to the bends.

43. The catheter of claim 39 wherein the positioning means further comprises:

a ferrule having a first end, a second end, an external surface, an internal surface, and a longitudinal axis extending from the first end to the second end;

an annular fulcrum positioned circumferentially on the midline of the length of the external surface of the ferrule and wherein the sensing position further comprises the sensing portion disposed outside the ferrule in an orientation generally parallel to the longitudinal axis of the ferrule and supported by the fulcrum of the ferrule, the fulcrum serving to position the sensing portion a distance beyond the external surface of the ferrule; and a stabilizing means for stably holding the sensing optical fiber.

44. The catheter of claim 43 wherein the stabilizing means further comprises a groove in the ferrule.

45. The catheter of claim 43 wherein the stabilizing means further comprises a nick in the fulcrum.

46. The catheter of claim 43 further comprising a depressing means disposed upon the positioning means generally near the sensing portion of the sensing optical fiber wherein when the flexible sleeve of the wall is compressed, the depressing means presses against the sensing portion.

47. The catheter of claim 39 wherein the positioning means further comprises:

rigid support means having an external surface; and a fulcrum positioned on the external surface of the rigid support means and wherein the sensing position further comprises the sensing portion disposed outside the rigid support means and supported by the fulcrum for positioning the sensing portion a distance beyond the external surface of the rigid support means.

48. The catheter of claim 47 further comprising a groove in the rigid support means for stabilizing the optical fiber.

49. The catheter of claim 47 further comprising a nick in the fulcrum for stabilizing the optical fiber.

* * * * *